United States Patent [19]

Markussen

[11] 4,343,898
[45] Aug. 10, 1982

[54] PROCESS FOR PREPARING ESTERS OF HUMAN INSULIN

[75] Inventor: Jan Markussen, Herlev, Denmark

[73] Assignee: Novo Industri A/S, Denmark

[21] Appl. No.: 233,051

[22] Filed: Feb. 10, 1981

[30] Foreign Application Priority Data

Feb. 11, 1980 [DK] Denmark .............................. 574/80
Aug. 28, 1980 [DK] Denmark ............................ 3662/80

[51] Int. Cl.$^3$ ............................................. C12P 21/04
[52] U.S. Cl. ......................................... 435/71; 435/70
[58] Field of Search ................ 260/112.7; 435/69, 70, 435/71

[56] References Cited

U.S. PATENT DOCUMENTS 3,276,961 10/1966 Bodanszky et al. .............. 260/112.7

OTHER PUBLICATIONS

Morihara et al.–Nature, vol. 280, Aug. 1979, pp. 412 & 413.
Inouye et al.–J.A.C.S., vol. 101, Jan. 1979, pp. 751 & 752.
Morihara–Hakka to Kogyo (Fermentation and Industry), vol. 38, No. 11 (1980), pp. 1052–1055.

*Primary Examiner*—Sam Rosen

[57] ABSTRACT

A process for converting insulin compounds containing the human insulin moiety

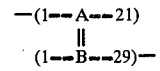

into h-In-Thr$^{B30}$ esters through transpeptidation of such insulin compounds with a threonine ester in solution of water and a water miscible solvent in the presence of trypsin and optionally an acid.

Yields in excess of 60% are obtained by limiting water content to less than 50% v/v of the reaction mixture and controlling reaction temperature, with below ambient temperature and extended reaction times being preferred.

A preferred starting material is the crude porcine insulin recovered from insulin salt cake and contaminated by proinsulin and degradation products thereof which contaminants convert into the h-In-Thr$^{B30}$ ester.

10 Claims, No Drawings

PROCESS FOR PREPARING ESTERS OF HUMAN INSULIN

This invention relates to conversion of insulin compounds into human insulin.

BACKGROUND OF THE INVENTION

In the treatment of diabetes mellitus insulin preparations derived from porcine or bovine insulin have generally been used. Bovine, porcine, and human insulins exhibit minor differences with respect to their amino acid sequence, the difference between human and porcine insulin being confined to a single amino acid in that the B30 amino acid of human insulin is threonine whereas that of porcine insulin is alanine. However, it could be argued that the ideal insulin preparation for human beings would be an insulin having exactly the same chemical structure as that of human insulin.

For the production of natural human insulin the necessary amount of human pancreas glands is not available.

Synthetic human insulin has been prepared on a small scale at great expense, vide Helv. Chim. Acta 57, 2617, and 60, 27.

Semisynthetic human insulin has been prepared from porcine insulin by what are believed to be tedious pathways, vide Hoppe-Zeyler's A. Physiol. Chem. 356, 1631, and Nature 280, 412.

One known semisynthetic process for preparing human insulin comprises the following three steps: First, porcine insulin is converted into porcine des-(Ala$^{B30}$)-insulin by treatment with carboxypeptidase A, vide Hoppe-Zeyler's A. Physiol. Chem. 359, 799. In the second step porcine des-(Ala$^{B30}$)-insulin is subjected to a trypsin-catalyzed coupling with Thr-OBu$^t$, whereby human insulin Thr$^{B30}$-tert-butyl ester is formed. Finally, said ester is treated with trifluoroacetic acid yielding human insulin, vide Nature 280, 412. The first step, however, results in a partial removal of Asn$^{A21}$, yielding des-(Ala$^{B30}$, Asn$^{A21}$)-insulin. This derivative gives, after the two subsequent reactions, rise to a contamination by des-(Asn$^{A21}$)-insulin in the semisynthetic human insulin product, a contamination which cannot easily be removed with known preparative methods. Des-(Asn$^{A21}$)-insulin possesses low biological activity (about 5%), vide Amer. J. Med. 40, 750.

U.S. Pat. No. 3,276,961 purports to relate to a transpeptidation process for preparing semisynthetic human insulin directly from porcine insulin. However, the yield of human insulin is poor because the process is performed in water, under which conditions trypsin causes splitting of the Arg$^{B22}$-Gly$^{B23}$ bond, vide J. Biol. Chem. 236, 743.

The invention is based upon the discovery that the amino acid or peptide chain bound to the carbonyl group of Lys$^{B29}$ in the insulin compound can be interchanged with a threonine ester. Said interchange is herein referred to as a transpeptidation.

The term "insulin compounds" as used herein encompasses insulins and insulin-like compounds containing the human des(Thr$^{B30}$) insulin moiety, the B30 amino acid of the insulin being alanine (in insulin from, e.g., hog, dog, and fin and sperm whale) or serine (rabbit). The term "insulin-like compounds" as used herein encompasses proinsulin derived from any of the above species and primates, together with intermediates from the conversion of proinsulin into insulin. As examples of such intermediates can be mentioned split proinsulin, desdipeptide propinsulins, desnonapeptide proinsulin, and diarginine insulins, vide R. Chance: In Proceedings of the Seventh Congress of IDF, Buenos Aires 1970, 292-305, Editors: R. R. Rodriques & J. V.-Owen, Excerpta Medica, Amsterdam.

One object of this invention is to provide a process for converting certain non-human insulins and insulin-like compounds into a threonine B30 ester of human insulin in high yields.

A second object of this invention is to provide a process for converting crude porcine insulin into a threonine B30 ester of human insulin in high yields.

BRIEF STATEMENT OF THE INVENTION

The process according to this invention comprises transpeptidizing an insulin compound or a salt or complex thereof with an excess of an L-threonine ester or a salt thereof in a mixture of water and a water miscible organic solvent in the presence of trypsin.

The reaction medium in which the threonine ester and insulin compounds are dissolved comprises water and a water miscible organic solvent, the water content of the reaction mixture being less than 50%, preferably 10–40% v/v. The reaction temperature range is from the freezing point of the reaction mixture to 50° C., but preferably is below ambient temperature. The preferred range is above 0° C. The reaction may require several days.

Optionally present in the reaction mixture is an acid, preferably an organic acid, in up to 10 equivalents per equivalent of the threonine ester.

A substantial excess of threonine ester is present in the reaction mixture solution, with the molar ratio of threonine ester to insulin compound preferably exceeding 5:1. The threonine ester concentration of the reaction mixture should preferably exceed 0.1 molar, with the upper concentration of the threonine ester being the solubility thereof.

To obtain the 60% transpeptidation yield considered herein as an important aspect to practice of this invention the reaction temperature, water content and acid content are interrelated within the described ranges. The attainment of high yields is positively correlated to low water concentration and presence of acid.

A preferred material for practice of this invention is crude porcine insulin. The insulin-like compounds present therein become converted into Thr$^{B30}$ ester of human insulin.

Under properly selected reaction conditions a yield exceeding 95% may be obtained from the transpeptidation reaction. If crude porcine insulin containing PLI (proinsulin-like immunoreactive compounds) is transpeptidized the PLI may be reduced by a factor of about 100, being advantageously converted into Thr$^{B30}$ ester of human insulin.

DISCUSSION OF THE INVENTION

As has already been pointed out the transpeptidation process of this invention is carried out in solution in a mixture of water and one or more water miscible organic solvents, and optionally, but preferably an acid.

The water content is held to less than 50% v/v of the reaction mixture.

The organic solvents suited to practice of this invention are polar solvents which are miscible with water and preferably such that are capable of containing therein high concentrations of insulin compounds and threonine ester. Examples of suitable organic solvents are aprotic solvents, such as N,N-dimethylformamide, N,N-dimethylacetamide, N-methylpyrrolidone, and hexamethylphosphortriamide, and protic solvents, such as ethanol, methanol, 2-propanol, and 1,2-ethanediol. Dioxane, acetone, tetrahydrofuran, formamide, and acetonitrile may also be used. The nature of the solvent does affect the system as a whole, and interrelationships suited to one solvent productive of high transpeptidation yields may not apply with a different solvent. Best yield results have been obtained with aprotic solvents, and aprotic solvents are most preferred for practice of this invention.

With the somewhat less preferred protic solvents, such as the alcohols, attainment of yields of 60% or more could be obtained by holding water content to below about 25% v/v and conducting the reaction at less than ambient temperature, vide infra.

The addition of an acid, such as hydrochloric, formic, acetic, propionic, or butyric acid, or of a base, such as pyridine, TRIS, N-methylmorpholine, or N-ethylmorpholine, is optional. They are included in the reaction mixture to bring about a suitable buffer system. Although mineral acids or bases may be used in practice of this invention organic acids and bases are preferred, particularly those identified above. Organic acids are most preferred. The acid content may range from zero to 10 equivalents per equivalent of threonine ester, and preferably 0.5–5 equivalents acid per equivalent of the ester. The threonine ester may be added to the reaction mixture as the free base. Better yields are obtained when an acid is added to the reaction mixture, the amount of acid needed for obtaining optimal yields being dependent on the choice of organic solvent. For example, with an aprotic solvent like N,N-dimethylacetamide high yields are obtained with about three mols of acetic acid per mol of threonine ester.

The transpeptidation of this invention is an enzymatic conversion catalyzed by trypsin. Although trypsin is best known for its proteolytic properties, workers in the art have recognized that trypsin is capable of catalyzing the coupling of des-(Ala$^{B30}$)-insulin and a threonine tert-butyl ester, see Nature 280, pp. 412–413 (Aug. 2, 1979). In the present process, the trypsin is used to catalyze a transpeptidation reaction at the Lys B29 carbonyl substituent, incorporating thereby a threonine ester as the B30 residue.

The trypsin type is not material to practice of this invention. Trypsin is a well characterized enzyme available in high purity, notably from bovine, porcine and some microbial species such as *Acromobacter lyticus*. Moreover, the trypsin form, whether it is native trypsin or an active immobilized trypsin or trypsin derivative is not material to practice of this invention. The term trypsin as employed herein is intended to include trypsins from all sources and all forms of trypsin that retain the transpeptidation activity herein employed. Ions which stabilize trypsin, e.g., calcium ions, may be present in the reaction mixture.

As examples of active trypsin derivatives can be mentioned acetylated trypsin, succinylated trypsin, glutaraldehyde treated trypsin, and immobilized trypsin derivatives.

If an immobilized trypsin is used it is suspended in the reaction medium.

To a great extent the action of trypsin is controlled by an interrelation of water and solvent content, the acid/base ratio, and the reaction temperature, so as to favor its transpeptidation action and to suppress undesired trypsin catalyzed side reactions. Increasing the concentration of organic solvent in the reaction mixture conduces to both but also increases the rate at which irreversible trypsin denaturation occurs. However, the latter may be at least partly counteracted by decreasing the reaction temperature. Reducing temperature also reduces the transpeptidation rate, but such reduction is compensated for by increasing reaction time. Since the denaturation rate is reduced more than the transpeptidation rate, conduct of the present process at below ambient temperature is advantageous. Temperatures above 0° C. are preferred and extended conversion times, e.g., 24–96 hours, may be advisable.

The weight ratio between trypsin (calculated as crystalline trypsin or an amount of trypsin derivative corresponding thereto) and the insulin compound in the reaction mixture is normally in the range of from 1:200 to 1:1, preferably above 1:50.

Inasmuch as high concentrations of insulin compound and of threonine ester in solution promote high conversion rates, solvent selection is biased towards those solvents in which the reactants, including insulin compounds, are very soluble. The solubility of the threonine ester in particular is important, because that reactant should be present in high concentration. The molar ratio of threonine ester to insulin compound should preferably exceed 5:1, the threonine ester concentration in the reaction mixture preferably being at least 0.1 molar.

The L-threonine esters contemplated for practice of this invention can be depicted by the following formula:

$$\text{Thr}(R^5)\text{—}OR^4 \qquad \text{II}$$

wherein $R^4$ represents a carboxyl protecting group, and $R^5$ represents hydrogen or a hydroxyl protecting group. Presence of a protecting group on the hydroxyl is optional.

Applicable threonine esters of the above formula II are such, in which $R^4$ is a carboxyl protecting group which can be removed from the human insulin ester under conditions, which do not cause substantial irreversible alterations in the insulin molecule. As examples of such carboxyl protecting groups can be mentioned lower alkyl, e.g., methyl, ethyl, and tert-butyl, substituted benzyl groups such as p-methoxybenzyl, diphenylmethyl, and 2,4,6-trimethylbenzyl, and groups of the general formula:

$$-CH_2-CH_2-SO_2R^6,$$

wherein $R^6$ represents lower alkyl, such as methyl, ethyl, propyl, and n-butyl.

Suitable hydroxyl protecting groups $R^5$ are those which can be removed from the human insulin ester under conditions which do not cause substantial irreversible alteration in the insulin molecule. As an example of such a group can be mentioned tert-butyl.

Further protection groups usually used are described by Wünch: Metoden der Organischen Chemie (Houben-Weyl), Vol. XV/1, editor: Eugen Müller, Georg Thieme Verlag, Stuttgart 1974.

Some compounds of the formula II are known compounds and the remaining compounds of formula II can be prepared in analogy with the preparation of known compounds or in analogy with known methods.

The threonine esters of formula II may be employed in the form of the free base or soluble salts thereof such as hydrochlorides, acetates, propionates, and butyrates.

Examples of a complex or salt of an insulin compound is a zinc complex or zinc salt.

The transpeptidation carried out by practice of this invention will, therefore, result in compounds of the formula:

$$(Thr(R^5)-OR^4)^{B30}\text{-h-In} \tag{III}$$

wherein -h-In designates human des-$(Thr^{B30})$-insulinyl, and $R^4$ and $R^5$ are as defined above.

Human insulin can be obtained from the above human insulin esters of the formula III by removal of the protecting group $R^4$ and any protecting group $R^5$ by known methods or methods known per se. In case $R^4$ is methyl, ethyl, or a group $$-CH_2-CH_2-SO_2R^6,$$

wherein $R^6$ is as defined above, the said protecting group can be removed at gentle basic conditions in an aqueous medium, preferably at a pH value of about 8–12, e.g., at about 9.5. As the base can be used ammonia, triethylamine, or hydroxides of alkali metals such as sodium hydroxide. In case $R^4$ is tert-butyl, substituted benzyl such as p-methoxybenzyl or 2,4,6-trimethylbenzyl, or diphenylmethyl, the said group can be removed by acidolysis, preferably with trifluoroacetic acid. The trifluoroacetic acid may be nonaqueous or may contain some water, or it may be diluted with an organic solvent, such as dichloromethane. In case $R^5$ is tert-butyl said group can be removed by acidolysis, vide above.

Preferred compounds of the formulae II and III are compounds wherein $R^5$ is hydrogen.

The conversion of insulin compounds into a $Thr^{B30}$ ester of human insulin can be visualized on the basis of the following formula assigned to the insulin compounds:

$$\begin{array}{c} R^1-(1\text{-}\text{-}A\text{-}\text{-}21) \\ \| \\ (1\text{-}\text{-}B\text{-}\text{-}29)-R^2 \end{array} \tag{I}$$

wherein $$\begin{array}{c} -(1\text{-}\text{-}A\text{-}\text{-}21) \\ \| \\ (1\text{-}\text{-}B\text{-}\text{-}29)- \end{array}$$

represents the human des($Thr^{B30}$)insulin moiety wherein $Gly^{A1}$ is connected to the substituent designated $R^1$ and $Lys^{B29}$ is connected to the substituent designated $R^2$, $R^2$ represents an amino acid or a peptide chain containing not more than 36 amino acids, and $R^1$ represents hydrogen or a group of the general formula $R^3-X-$, wherein X represents arginine or lysine, and $R^3$ represents a peptide chain containing not more than 35 amino acids, or $R^2$ together with $R^3$ represent a peptide chain containing not more than 35 amino acids, with the proviso that the number of amino acids present in $R^1$ plus $R^2$ is less than 37.

Thus, the transpeptidation of this invention converts any of the above insulin compounds into threonine$^{B30}$ esters of human insulin (formula III), which then can be deblocked to form human insulin.

A further advantage of this invention is that insulin-like compounds present in crude insulin and present in some commercial insulin preparations and covered by the formula I by the transpeptidation of this invention are converted into threonine$^{B30}$ esters of human insulin, which then can be deblocked to form human insulin. Examples of insulin-like compounds of formula I appear from the following:

Porcine diarginine insulin ($R^1$ is hydrogen, and $R^2$ is -Ala-Arg-Arg), porcine proinsulin ($R^1$ together with $R^2$ is -Ala-Arg-Arg-Glu-Ala-Glu-Asn-Pro-Gln-Ala-Gly-Ala-Val-Glu-Leu-Gly-Gly-Gly-Leu-Gly-Gly-Leu-Gln-Ala-Leu-Ala-Leu-Glu-Gly-Pro-Pro-Gln-Lys-Arg-, wherein the terminal alanyl is connected to $Lys^{B29}$), dog proinsulin ($R^1$ together with $R^2$ is -Ala-Arg-Arg-Asp-Val-Glu-Leu-Ala-Gly-Ala-Pro-Gly-Glu-Gly-Gly-Leu-Gln-Pro-Leu-Ala-Leu-Glu-Gly-Ala-Leu-Gln-Lys-Arg-, wherein the terminal alanyl is connected to $Lys^{B29}$), porcine split proinsulin ($R^1$ is Ala-Leu-Glu-Gly-Pro-Pro-Gln-Lys-Arg-, and $R^2$ is -Ala-Arg-Arg-Glu-Ala-Glu-Asn-Pro-Gln-Ala-Gly-Ala-Val-Glu-Leu-Gly-Gly-Gly-Leu-Gly-Gly-Leu-Gln-Ala-Leu), porcine desdipeptide proinsulin ($R^1$ is hydrogen, and $R^2$ is -Ala-Arg-Arg-Glu-Ala-Glu-Asn-Pro-Gln-Ala-Gly-Ala-Val-Glu-Leu-Gly-Gly-Gly-Leu-Gly-Gly-Leu-Gln-Ala-Leu-Ala-Leu-Glu-Gly-Pro-Pro-Gln), human proinsulin ($R^1$ together with $R^2$ is -Thr-Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-, wherein the terminal threonyl is connected to $Lys^{B29}$), and monkey proinsulin ($R^1$ together with $R^2$ is -Thr-Arg-Arg-Glu-Ala-Glu-Asp-Pro-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg-, wherein the terminal threonyl is connected to $Lys^{B30}$).

Hence, in all these insulin-like compounds covered by formula I the $R^1$ substituent designated $R^3-X-$ is exchanged with hydrogen.

Preferred practice of this invention is, therefore, to carry out the transpeptidation process on a crude porcine insulin material, e.g., on crude insulin inwhatever form is recovered from the pancreas glands, optionally via a salt cake, vide Ind. Eng. Chem. 32, 908–910. Thus, citrate crystals, a well known form of crude porcine insulin constitutes a preferred reactant in practice of this invention. The conversion of insulin-like compounds that heretofore had to be removed and discarded in preparation of insulin with no or very low antigenic properties is believed to be a special advantage to practice of this invention.

The process according to the present invention has, therefore, the following advantages over the prior art:

(a) The enzymatic hydrolysis to remove $Ala^{B30}$, e.g., with carboxypeptidase A, is avoided.

(b) The isolation of intermediate compound, such as porcine des-($Ala^{B30}$)-insulin, is unnecessary.

(c) Contamination with des-($Asn^{A21}$)-insulin derivatives is avoided.

(d) Proinsulin and other insulin-like compounds present in crude insulin are—via the threonine$^{B30}$ ester of human insulin—converted into human insulin by the process of this invention, whereby the yield is increased.

(e) Antigenic insulin-like compounds, vide British Pat. No. 1,285,023, are converted into human insulin.

When selecting the reaction conditions according to the above explanation and considering the results obtained in the following examples it is possible to obtain a yield of threonine$^{B30}$ ester of human insulin which is higher than 60%, and even higher than 80%, and under certain preferred conditions higher than 90%.

A preferred procedure for preparing human insulin is as follows:

(1) The starting material used for the transpeptidation is crude porcine insulin, e.g., crystalline insulin obtained by the use of a citrate buffer, vide U.S. Pat. No. 2,626,228.

(2) If there is any trypsin activity left after the transpeptidation, it is preferred to remove it, e.g., under conditions where trypsin is inactive, e.g., in acid medium below pH 3. Trypsin can be removed by separation according to molecular weight, e.g., by gel filtration on "Sephadex G-50" or "Bio-gel P-30" in 1 M acetic acid, vide Nature 280, 412.

(3) Other impurities such as unreacted porcine insulin may be removed by the use of anion and/or cation exchange chromatography, vide Examples 1 and 2 herein.

(4) Thereafter, the threonine$^{B30}$ ester of human insulin is deblocked and human insulin is isolated, e.g., crystallized, in a manner known per se.

By this process human insulin of an acceptable pharmaceutical purity can be obtained and be further purified, if desired.

Abbreviations used are in accordance with the rules approved (1974) by the IUPAC-IUB Commission on Biochemical Nomenclature, vide Collected Tentative Rules & Recommendations of the Commission on Biochemical Nomenclature IUPAC-IUB, 2nd ed., Maryland 1975.

For further understanding of this invention there follows numerous examples, prefaced by a description of the analytic procedures used to ascertain the results provided in the examples.

ANALYTICAL TESTS

The conversion of porcine insulin and porcine proinsulin into human insulin esters can be demonstrated by DISC PAGE electrophoresis in 7.5% polyacrylamide gel in a buffer consisting of 0.375 M Tris, 0.06 M HCl, and 8 M urea. The pH of the buffer is 8.7. Esters of the formula III migrate with a speed of 75% of that of porcine insulin. Porcine proinsulin migrating with 55% of the speed of porcine insulin is by the process according to the present invention converted into the same product. Identification of the conversion product as compounds of the formula III is due to the following criteria:

(a) The electrophoretic migration of the human insulin esters of formula III in relation to porcine insulin corresponds to the loss of one negative charge.

(b) The amino acid composition of the stained protein bonds in the gel representing compounds of the formula III is identical with that of human insulin, i.e. 3 mol threonine and 1 mol alanine per mol insulin, and the composition of porcine insulin is 2 mol threonine and 2 mol alanine per mol insulin. The technique for analyzing amino acid compositions of protein bonds in polyacrylamide gels has been described in Eur. J. Biochem. 25, 147.

(c) The proof that the incorporated threonine is placed as C-terminal amino acid in the B chain, is proved by oxidative sulfitolysis of the S-S bridges of insulin in 6 M guanidinium hydrochloride followed by separation of A and B chains by ion exchange chromatography on "SP Sephadex". Digestion of the B chain S-sulfonate with carboxypeptidase A liberates only the C-terminal amino acid. The technique has been described by Markussen in Proceedings of the Symposium on Proinsulin, Insulin and C-peptide, Tokushima, July 12-14, 1978, (Editor: Baba, Kaneko & Yaniahara) Int. Congress Series No. 468, Excerpta Medica, Amsterdam-Oxford. The analysis is performed after the ester group has been split from compounds of the formula III.

Those three analyses prove unambiguously that the conversion into human insulin has taken place.

The conversion of porcine insulin and porcine proinsulin into human insulin esters can be followed quantitatively by HPLC (high pressure liquid chromatography) on reverse phase. A4×300 mm "µBondapak $C_{18}$ column" (Waters Ass.) was used and the elution was performed with a buffer comprising 0.2 M ammonium sulphate (adjusted to a pH value of 3.5 with sulphuric acid) and containing 26-50% acetonitrile. The optimal acetonitrile concentration depends on which ester of the formula III one desires to separate from porcine insulin. In case $R^4$ is methyl, and $R^5$ is hydrogen, separation is achieved in 26% (v/v) of acetonitrile. Porcine insulin and (Thr-OMe)$^{B30}$-h-In (Me is methyl) elute after 4.5 and 5.9 column volumes, respectively, as well separated symmetrical peaks. Before the application on the HPLC column the proteins in the reaction mixture were precipitated by addition of 10 volumes of acetone. The precipitate was isolated by centrifugation, dried in vacuo, and dissolved in 0.02 M sulphuric acid.

The process for preparing human insulin esters and human insulin is illustrated by the following examples which, however, are not to be construed as limiting. The examples illustrate some preferred embodiments of the process according to the invention.

EXAMPLE 1

200 mg crude porcine insulin, crystallized once, was dissolved in 1.8 ml 3.33 M acetic acid. 2 ml of a 2 M solution of Thr-OMe (Me is methyl) in N,N-dimethylacetamide, and 20 mg of trypsin dissolved in 0.2 ml of water were added. After storage for 18 hours at 37° C. the proteins were precipitated by the addition of 40 ml of acetone, and the precipitate was isolated by centrifugation. The supernatent was discarded. Analysis of the precipitate by HPLC using 26% acetonitrile (vide Analytical tests) showed a 60% conversion of porcine insulin into (Thr-OMe)$^{B30}$-h-In. The precipitate was dissolved in 8 ml freshly deionized 8 M urea, the pH value was adjusted to 8.0 with 1 M ammonia, and the solution was applied to a 2.5×25 cm column packed with "QAE A-25 Sephadex", equilibrated with a 0.1 M ammonium chloride buffer, which contained 60% (v/v) ethanol, the pH value of which was adjusted to 8.0 with ammonia. Elution was carried out with the same buffer, and fractions of 15 ml were collected. (Thr-OMe)$^{B30}$-h-In was found in the fractions Nos. 26-46, and unreacted porcine insulin in the fractions Nos. 90-120. The fractions Nos. 26-46 were pooled, the ethanol evaporated in vacuo, and the (Thr-OMe)$^{B30}$-h-In was crystallized in a citrate buffer as described by Schlichtkrull et al., Handbuch der inneren Medizin, 7/2A, 96, Berlin, Heidelberg, New York 1975. The yield was 95 mg of crystals having the same rhombic shape as porcine insulin crystallized in the same manner. The amino acid composition was found to be identical with that of human insulin. Further analytical tests described in the above section: "Analytical Tests", prooved that the resulting product was (Thr-OMe)$^{B30}$-h-In.

EXAMPLE 2

100 mg porcine insulin fulfilling the purity requirements stated in British Pat. No. 1,285,023 was dissolved in 0.9 ml 3.33 M acetic acid and, thereafter, 1 ml of a 2 M solution of threonine methyl ester in N,N-dimethylformamide and 12 mg TPCK (tosylphenylalaninchloromethylketone) treated trypsin dissolved in 0.1 ml water were added. After an incubation for 24 hours at 37° C. the reaction was stopped by the addition of 4 ml 1 M phosphoric acid. The (Thr-OMe)$^{B30}$-h-In obtained was separated from non-reacted porcine insulin by ion exchange chromatography on a 2.5×25 cm column of "SP-Sephadex" with an eluent comprising 0.09 M sodium chloride and 0.02 M sodium dihydrogen phosphate (pH value of the buffer: 5.5) in 60% ethanol. Fractions containing (Thr-OMe)$^{B30}$-h-In were collected, the ethanol was removed in vacuo, and the product was crystallized as described in Example 1. The yield was 50 mg of (Thr-OMe)$^{B30}$-h-In.

EXAMPLE 3

100 mg porcine proinsulin was dissolved in 0.9 ml of 3.33 M acetic acid and converted into (Thr-OMe)$^{B30}$-h-In and purified as described for porcine insulin in Example 1. The conversion of proinsulin into (Thr-OMe)$^{B30}$-h-In was found to be 73% by HPLC analysis of the acetone precipitate. The yield of crystalline (Thr-OMe)$^{B30}$-h-In was 54 mg.

EXAMPLE 4

100 mg porcine insulin was dissolved in 0.9 ml of 2.77 M acetic acid in water and reacted analogically to the process described in Example 2. After completion of the reaction the proteins were precipitated by the addition of 10 volumes of acetone. Analysis by DISC PAGE showed a conversion into (Thr-OMe)$^{B30}$-h-In of 70%.

EXAMPLE 5

100 mg porcine insulin was dissolved in 0.9 ml of 3.33 M acetic acid and 1 ml 2 M Thr-OMe in N-methylpyrrolidone was added. The reaction was performed in a manner analogous to that described in Example 4 and the convertion into (Thr-OMe)$^{B30}$-h-In was 20%.

EXAMPLE 6

100 mg porcine insulin was dissolved in 0.9 ml of 2.77 M acetic acid in water and 1 ml 2 M Thr-OMe in HMPA (hexamethylphosphortriamide) was added. The reaction was performed in a manner analogous to that described in Example 4. The convertion into (Thr-OMe)$^{B30}$-h-In was 80%.

EXAMPLE 7

100 mg porcine insulin was dissolved in 0.9 ml of 3.33 M acetic acid and 1 ml 2 M Thr-OMe in N,N-dimethylacetamide was added. The reaction was performed in a manner analogous to that described in Example 4. The convertion into (Thr-OMe)$^{B30}$-h-In was 80%.

EXAMPLE 8

100 mg porcine insulin was dissolved in 0.9 ml of 3.33 M acetic acid and 1 ml 2 M Thr-OMe in N,N-dimethylacetamide was added. Thereafter, 200 U trypsin activity (measured against the substrate BAEE) immobilized on 1 g of glass beads was added and after incubation at 37° C. during 24 hours the trypsin bound to the glass was filtered off. After completion of the reaction the proteins were precipitated by the addition of 10 volumes of acetone. Analysis by DISC PAGE showed a conversion into (Thr-OMe)$^{B30}$-h-In of 40%.

EXAMPLE 9

100 mg porcine insulin was dissolved in 0.9 ml of 3.33 M acetic acid and 1 ml 2 M Thr-OMe in N,N-dimethylacetamide was added. Thereafter, 300 U trypsin (activity measured with the substrate BAEE) immobilized on 200 μg CNBr activated "Sephadex G-150" was added. After incubation at 37° C. during 24 hours the trypsin bound to "Sephadex" was filtered off. After completion of the reaction the proteins were precipitated by the addition of 10 volumes of acetone. Analysis by DISC PAGE showed a conversion into (Thr-OMe)$^{B30}$-h-In of 70%.

EXAMPLE 10

The process described in Example 7 was repeated, provided that the ester used was 2 M Thr-OBu$^t$ (Bu$^t$ is tert-butyl) in N,N-dimethylacetamide. The convertion into (Thr-OBu$^t$)$^{B30}$-h-In was 80%.

EXAMPLE 11

The process described in Example 8 repeted, provided that the ester used was 2 M Thr-OBu$^t$ in N,N-dimethylacetamide. The convertion into (Thr-OBu$^t$)$^{B30}$-h-In was 30%.

EXAMPLE 12

The process described in Example 9 was repeted, provided that the ester used was 2 M Thr-OBu$^t$ in N,N-dimethylacetamide. The convertion into (Thr-OBu$^t$)$^{B30}$-h-In was 70%.

EXAMPLE 13

100 mg porcine proinsulin was dissolved in 0.9 of 3.33 M acetic acid and 1 ml 2 M Thr-OMe in N,N-dimethylacetamide was added. The reaction was performed in a manner analogous to that described in Example 4. The convertion into (Thr-OMe)$^{B30}$-h-In was 80%.

EXAMPLE 14

100 mg porcine proinsulin was dissolved in 0.9 ml of 3.33 M acetic acid and 1 ml 2 M Thr-OMe in N,N-dimethylacetamide was added. The mixture was treated with immobilized trypsin analogically to the process described in Example 8. Thr convertion into (Thr-OMe)$^{B30}$-h-In was 40%.

EXAMPLE 15

100 mg porcine proinsulin was dissolved in 0.9 ml of 3.33 M acetic acid and 1 ml 2 M Thr-OMe in N,N-dimethylacetamide was added. The mixture was treated analogically to the process described in Example 9 with immobilized trypsin. The convertion into (Thr-OMe)$^{B30}$-h-In was 70%.

EXAMPLE 16

100 mg porcine proinsulin was dissolved in 0.9 ml of 3.33 M acetic acid and 1 ml 2 M Thr-OBu$^t$ in N,N-dimethylacetamide was added. The reaction was performed in a manner analogous to that described in Example 4. The convertion into (Thr-OBu$^t$)$^{B30}$-h-In was 80%.

EXAMPLE 17

100 mg porcine proinsulin was dissolved in 0.9 ml of 3.33 M acetic acid and 1 ml 2 M Thr-OBu$^t$ in N,N-dimethylacetamide was added. The mixture was treated with trypsin immobilized to glass beads analogically to process described in Example 8. The convertion into (Thr-OBu$^t$)$^{B30}$-h-In was 40%.

EXAMPLE 18

100 mg porcine proinsulin was dissolved in 0.9 ml of 3.33 M acetic acid and 1 ml 2 M Thr-OBu$^t$ in N,N-dimethylacetamide was added. The mixture was treated with trypsin immobilized to CNBr activated "Sephadex G-150" analogically with the process described in Example 9. The convertion into (Thr-OBu$^t$)$^{B30}$-h-In was 70%.

EXAMPLE 19

100 mg porcine insulin was dissolved in 0.5 ml of 6 M acetic acid and 1 ml 1 M Thr-OTmb (Tmb is 2,4,6-trimethylbenzyl) in N,N-dimethylacetamide was added. Furthermore, 0.5 ml N,N-dimethylacetamide and 5 mg TPCK treated trypsin in 0.1 ml water were added. The reaction mixture was stored at 32° C. for 44 hours. After completion of the reaction the proteins were precipitated by the addition of 10 volumes of acetone. Analysis by DISC PAGE showed a conversion into (Thr-OTmb)$^{B30}$-h-In of 50%.

EXAMPLE 20

100 mg porcine insulin was dissolved in 0.9 ml of 3 M acetic acid and 1 ml 2 M Thr-OMe in dioxane was added. The reaction was performed in a manner analogous to that described in Example 4 and the conversion into (Thr-OMe)$^{B30}$-h-In was 10%.

EXAMPLE 21

100 mg porcine insulin was dissolved in 0.9 ml of 3 M acetic acid and 1 ml 2 M Thr-OMe in acetonitrile was added. The reaction was performed in a manner analogous to that described in Example 4 and the conversion into (Thr-OMe)$^{B30}$-h-In was 10%.

EXAMPLE 22

250 mg of crystalline (Thr-OMe)$^{B30}$-h-In was dispersed in 25 ml of water and dissolved by the addition of 1 N sodium hydroxide solution to a pH value of 10.0. The pH value was kept constant at 10.0 for 24 hours at 25° C. The human insulin formed was crystallized by the addition of 2 g of sodium chloride, 350 mg of sodium acetate trihydrate and 2.5 mg of zinc acetate dihydrate followed by the addition of 1 N hydrochloric acid to obtain a pH value of 5.52. After storage for 24 hours at 4° C. the rhombohedral crystals were isolated by centrifugation, washed with 3 ml of water, isolated by centrifugation, and dried in vacuo. Yield: 220 mg of human insulin.

EXAMPLE 23

100 mg (Thr-OTmb)$^{B30}$-h-In was dissolved in 1 ml of ice cold trifluoroacetic acid and the solution was stored for 2 hours at 0° C. The human insulin formed was precipitated by the addition of 10 ml of tetrahydrofuran and 0.97 ml of 1.03 M hydrochloric acid in tetrahydrofuran. The precipitate formed was isolated by centrifugation, washed with 10 ml of tetrahydrofuran, isolated by centrifugation, and dried in vacuo. The precipitate was dissolved in 10 ml of water and the pH value of the solution was adjusted to 2.5 with 1 N sodium hydroxide solution. The human insulin was precipitated by the addition of 1.5 g of sodium chloride and isolated by centrifugation. The precipitate was dissolved in 10 ml of water, and the human insulin was precipitated by the addition of 0.8 g of sodium chloride, 3.7 mg of zinc acetate dihydrate and 0.14 g of sodium acetate trihydrate followed by the addition of 1 N sodium hydroxide solution to obtain a pH value of 5.52. After storage for 24 hours at 4° C., the precipitate was isolated by centrifugation, washed with 0.9 ml of water, isolated by centrifugation and dried in vacuo. Yield: 90 mg of human insulin.

EXAMPLE 24

100 mg of porcine insulin was dissolved in 0.5 ml of 10 M acetic acid and 1.3 ml of 1.54 M Thr-OMe in N,N-dimethylacetamide was added. The mixture was cooled to 12° C. 10 mg of trypsin dissolved in 0.2 ml of 0.05 M calcium acetate was added. After 48 hours at 12° C. the proteins were precipitated by addition of 20 ml of acetone. The conversion of porcine insulin into (Thr-OMe)$^{B30}$-h-In was 97% by HPLC.

EXAMPLE 25

20 mg of porcine insulin was dissolved in a mixture of 0.08 ml of 10 M acetic acid and 0.14 ml of water. 0.2 ml of 2 M Thr-OMe in N,N-dimethylacetamide was added and the mixture was cooled to −10° C. 2 mg of trypsin dissolved in 0.025 ml of 0.05 M calcium acetate was added. After 72 hours at −10° C. the proteins were precipitated by addition of 5 ml of acetone. The conversion of porcine insulin into (Thr-OMe)$^{B30}$-h-In was 64% by HPLC.

EXAMPLE 26

20 mg of porcine insulin was dispensed in 0.1 ml of water. Addition of 0.6 ml of 2 M Thr-OMe in N,N-dimethylacetamide caused the insulin to go into solution. The mixture was cooled to 7° C. 2 mg of trypsin dissolved in 0.025 ml of 0.05 M calcium acetate was added. After 24 hours at 7° C. the proteins were precipitated by addition of 5 ml of acetone. The conversion of porcine insulin into (Thr-OMe)$^{B30}$-h-In was 62% by HPLC.

EXAMPLE 27

20 mg of porcine insulin was dissolved in 0.135 ml of 4.45 M propionic acid. 0.24 ml of 1.67 M Thr-OMe in N,N-dimethylacetamide was added. 2 mg of trypsin in 0.025 ml of 0.05 M calcium acetate was added and the mixture was kept at 37° C. for 24 hours. The proteins were precipitated by addition of 10 volumes of 2-propanol. The conversion of porcine insulin into (Thr-OMe)$^{B30}$-h-In was 75% by HPLC.

EXAMPLE 28

20 mg of porcine insulin was dispersed in 0.1 ml of water. 0.4 ml 2 M Thr-OMe in N,N-dimethylacetamide was added followed by 0.04 ml of 10 N hydrochloric acid caused the insulin to go into solution. 2 ml of trypsin dissolved in 0.025 ml of 0.05 M calcium acetate was added and the mixture was kept at 37° C. for 4 hours. Analysis by HPLC showed a 46% conversion of porcine insulin into (Thr-OMe)$^{B30}$-h-In.

EXAMPLE 29

20 mg of porcine insulin was dissolved in 0.175 ml of 0.57 M acetic acid. 0.2 ml of 2 M Thr-OMe in N,N-dimethylacetamide was added followed by the addition of 0.025 ml of 0.05 M calcium acetate. 10 mg of a crude preparation of *Achromobacter lyticus* protease was added and the mixture was kept for 22 hours at 37° C. The proteins were precipitated by the addition of 10 volumes of acetone. The conversion of porcine insulin into (Thr-OMe)$^{B30}$-h-In was 12% by HPLC.

EXAMPLE 30

20 mg of porcine insulin was dispersed in 0.1 ml of 0.5 M acetic acid. Addition of 0.2 ml of 0.1 M Thr-OMe in N,N-dimethylacetamide dissolved the insulin. The mixture was cooled to 12° C. and 2 mg of trypsin in 0.025 ml of 0.05 M calcium acetate was added. After 24 hours at 12° C. the analysis by HPLC showed a 42% conversion of porcine insulin into (Thr-OMe)$^{B30}$-h-In.

EXAMPLE 31

2 mg of rabbit insulin was dissolved in 0.135 ml of 4.45 M acetic acid. 0.24 ml of 1.67 M Thr-OMe in N,N-dimethylacetamide was added followed by the addition of 1.25 mg trypsin in 0.025 ml of 0.05 M calcium acetate. The mixture was kept at 37° C. for 4 hours. Analysis by HPLC showed an 88% conversion of rabbit insulin into (Thr-OMe)$^{B30}$-h-In. Rabbit insulin elutes before porcine insulin from the HPLC column, the ratio between the elution volumes of rabbit insulin to (Thr-OMe)$^{B30}$-h-In being 0.72.

EXAMPLE 32

2 mg of porcine diarginine insulin (Arg$^{B31}$-Arg$^{B32}$-insulin) was dissolved in 0.135 ml of 4.45 M acetic acid. 0.24 ml of 1.67 M Thr-OMe in N,N-dimethylacetamide was added followed by the addition of 1.25 mg of trypsin in 0.025 ml of 0.05 M calcium acetate. The mixture was kept at 37° C. for 4 hours. Analysis by HPLC showed a 91% conversion of diarginine insulin into (Thr-OMe)$^{B30}$-h-In. Diarginine insulin elutes before porcine insulin from the HPLC column, the ratio between the elution volumes of diarginine insulin to (Thr-OMe)$^{B30}$-h-In being 0.50.

EXAMPLE 33

2 mg of porcine intermediates (i.e. a mixture of desdipeptide (Lys$^{62}$-Arg$^{63}$)proinsulin and desdipeptide(Arg$^{31}$-Arg$^{32}$)proinsulin) was reacted analogously to the reaction described in Example 32. Analysis by HPLC showed 88% (Thr-OMe)$^{B30}$-h-In.

EXAMPLE 34

20 mg of porcine insulin was dissolved in 0.1 ml of 2 M acetic acid. 0.2 ml of 2 M Thr-OMe in N,N-dimethylacetamide was added and the mixture was cooled to −18° C. 2 mg of trypsin dissolved in 0.025 ml of 0.05 M calcium acetate was added and the mixture was kept for 120 hours at −18° C. Analysis by HPLC showed that the conversion into (Thr-OMe)$^{B30}$-h-In was 83%.

EXAMPLE 35

The process described in Example 34 was repeted with the proviso that the reaction was carried out at 50° C. for 4 hours. Analysis by HPLC showed that the conversion into (Thr-OMe)$^{B30}$-h-In was 23%.

EXAMPLE 36

20 mg of porcine insulin was dissolved in 0.1 ml of 3 M acetic acid. 0.3 ml of 0.33 M Thr-O(CH$_2$)$_2$—SO$_2$—CH$_3$, CH$_3$COOH (threonine 2-(methylsulfonyl)ethylester, hydroacetate) in N,N-dimethylacetamide was added. The mixture was cooled to 12° C. and 2 mg of trypsin in 0.025 ml of 0.05 M calcium acetate was added. HPLC showed after 24 hours at 12° C. a 77% conversion into (Thr-O(CH$_2$)$_2$—SO$_2$—CH$_3$)$^{B30}$-h-In. The product elutes approximately at the position of (Thr-OMe)$^{B30}$-h-In.

EXAMPLE 37

20 mg of porcine insulin was dissolved in 0.1 ml of 10 M acetic acid. 0.2 ml of 2 M Thr-OEt (Et is ethyl) in N,N-dimethylacetamide was added and the mixture was cooled to 12° C. 2 mg of trypsin in 0.025 ml of 0.05 M calcium acetate was added. HPLC showed after 24 hours at 12° C. a 75% conversion into (Thr-OEt)$^{B30}$-h-In. The product eluted in a portion slightly after that of (Thr-OMe)$^{B30}$-h-In.

EXAMPLE 38

20 mg of porcine insulin was dissolved in 0.1 ml of 6 M acetic acid. 0.3 ml of 0.67 M Thr(Bu$^t$)-OBu$^t$ (Bu$^t$ is tertiary butyl) in N,N-dimethylacetamide was added. The mixture was cooled to 12° C. and 2 mg of trypsin in 0.025 ml of 0.05 M calcium acetate was added. After 24 hours at 12° C. the conversion into (Thr(Bu$^t$)-OBu$^t$)$^{B30}$-h-I was 77%. The product was eluted from the HPLC column by applying a gradient in acetonitrile from 27% to 40%.

EXAMPLE 39

20 mg of porcine insulin was dissolved in 0.1 ml of 4 M acetic acid. 0.2 ml of 1.5 M Thr-OMe dissolved in tetrahydrofuran was added and the mixture was cooled to 12° C. 2 mg of trypsin dissolved in 0.025 ml of 0.05 M calcium acetate was added. After 4 hours at 12° C. the analysis by HPLC showed a conversion of 75% into (Thr-OMe)$^{B30}$-h-I.

EXAMPLE 40

20 mg of porcine insulin was dissolved in 0.1 ml of 4 M acetic acid. 0.8 ml of 2 M Thr-OMe dissolved in 1,2-ethanediol was added and the mixture was cooled to 12° C. 2 mg of trypsin dissolved in 0.025 ml of 0.05 M calcium acetate was added. After 4 hours at 12° C. the analysis by HPLC showed a conversion of 48% into (Thr-OMe)$^{B30}$-h-I.

EXAMPLE 41

20 mg of porcine insulin was dissolved in 0.1 ml of 4 M acetic acid. 0.2 ml of 2 M Thr-OMe dissolved in ethanol was added and the mixture was cooled to 12° C. 2 mg of trypsin dissolved in 0.025 ml of 0.05 M calcium acetate was added and the reaction was carried out for 4 hours at 12° C. Analysis by HPLC showed a 46% conversion into (Thr-OMe)$^{B30}$-h-In.

EXAMPLE 42

20 mg of porcine insulin was dissolved in 0.1 ml of 4 M acetic acid. 0.2 ml of 2 M Thr-OMe in acetone was added and the mixture was cooled to 12° C. 2 mg of trypsin dissolved in 0.025 ml of 0.05 M calcium acetate was added. After 4 hours at 12° C. the analysis by HPLC showed a conversion of 48% into (Thr-OMe)$^{B30}$-h-In.

I claim:
1. In a process for preparing human insulin, the improvement which comprises transpeptidizing into a human insulin Thr$^{B30}$-ester in high yield an insulin compound or a salt or complex thereof convertible into a human insulin Thr$^{B30}$-ester by reacting a non-Thr$^{B30}$- ester insulin compound or salt or complex thereof with an L-threonine ester or a salt thereof in a mixture of water and a water miscible organic solvent, in the presence of trypsin, and in the optional presence of up to 10 equivalents of acid per equivalent of the L-threonine ester, the content of water in the reaction solution exceeding about 10% and being less than 50% v/v, and the reaction temperature being below 50° C.

2. The process of claim 1 wherein the insulin compound is a relatively crude form of porcine insulin.

3. The process of claim 1 wherein the weight ratio between trypsin and the insulin compound in the reaction mixture is between 1:200 and 1:1.

4. The process of claim 1 wherein the acid content exceeds 0.5 equivalents per equivalent of L-threonine ester and the acid, water and solvent proportions and the reaction temperature are interrelated so as to achieve a transpeptidation yield exceeding about 60%.

5. In a process for preparing human insulin the improvement which comprises transpeptidizing into $Thr^{B30}$-esters of human insulin in high yield an insulin compound selected from the group consisting of porcine, dog, fin-whale, or sperm-whale insulin, rabbit insulin, porcine diarginine insulin, porcine proinsulin, dog proinsulin, porcine split proinsulin, porcine desdipeptide proinsulin, human proinsulin, and monkey proinsulin and mixtures thereof with a L-threonine ester in mixture of water, a water miscible organic solvent, in the presence of trypsin, and in the optional presence of up to 10 equivalents of acid per equivalent of the L-threonine ester, the content of water in the reaction solution exceeding about 10% and being less than 50% v/v, the content of L-threonine ester exceeding 0.1 molar, the reaction temperature being below 50° C.

6. In a process for converting porcine insulin into human insulin the improvement which comprises transpeptidizing a crude porcine insulin into $Thr^{B30}$-ester of human insulin in high yield with a L-threonine ester in a mixture of water and an aprotic solvent, in the presence of trypsin and optionally in the presence of up to 10 equivalents of an organic acid per equivalent of L-threonine ester, the content of water in the reaction mixture exceeding about 10% and being less than 50% v/v, the concentration of L-threonine ester exceeding 0.1 molar in the reaction mixture and exceeding a 5:1 molar ratio relative to the insulin, at temperatures less than about 50° C. whereby porcine insulin and insulin-like compounds present in said crude insulin become converted into $Thr^{B30}$-esters of human insulin.

7. The process of claim 6 wherein the water content is between 40 and 10% v/v, the organic acid content is in the range of 0.5-5 equivalents per equivalent of L-threonine ester, and the transpeptidation is carried out at a temperature below ambient temperature.

8. The process of claim 7 wherein the L-threonine ester concentration exceeds 0.1 molar and the reaction temperature is between 0° C. and ambient temperature.

9. The process of claim 8 wherein the weight ratio between trypsin and the crude porcine insulin is between 1:200 and 1:1.

10. The process of claim 6 including the steps of:
 thereafter separating unreacted porcine insulin from the threonine$^{B30}$ ester of human insulin, then cleaving the ester blocking group, and thereafter isolating the human insulin.

* * * * *